US00PP13309P2

(12) United States Plant Patent
Clark et al.

(10) Patent No.: US PP13,309 P2
(45) Date of Patent: Dec. 3, 2002

(54) GRAPEVINE PLANT NAMED 'JUPITER'

(75) Inventors: John Reuben Clark, Fayetteville, AR (US); James Norman Moore, Fayetteville, AR (US)

(73) Assignee: University of Arkansas, Fayetteville, AR (US)

( * ) Notice: Subject to any disclaimer, the term of this patent is extended or adjusted under 35 U.S.C. 154(b) by 0 days.

(21) Appl. No.: 09/228,491

(22) Filed: Jan. 11, 1999

(51) Int. Cl.[7] ..... A01H 5/00

(52) U.S. Cl. ..... Plt./205

(58) Field of Search ..... Plt./205

(56) References Cited

PUBLICATIONS

Frequently asked questions about Color Physics. Internet. http://www.geog.ucsb.edu/~jeff/115a/younghemltheory.html p. 7, 2000.*

Section 503 Application No. and Filing Receipt. MPEP. pp. 500–9, 500–11, Jul. 1998.*

* cited by examiner

*Primary Examiner*—Bruce R. Campell
*Assistant Examiner*—Michelle Kizilkaya

(57) ABSTRACT

Description and specifications of a new and distinct grapevine variety which originated from a hand-pollinated cross of Arkansas Selection 1258 (non Patented) and Arkansas Selection 1672 (non Patented) are provided. This new grapevine variety can be distinguished by its large seedless fruit, excellent muscat flavor, resistance to fruit cracking, good productivity, and good vine hardiness.

2 Drawing Sheets

SUMMARY OF THE INVENTION

The new and distinct variety of grapevine originated from a hand-pollinated cross of Arkansas Selection 1258 (non-patented)×Arkansas Selection 1672 (non-patented) made in 1981 at the Arkansas Agricultural Experiment Station Fruit Substation at Clarksville, Ark. Arkansas selection 1258 is a seeded, red-fruited grape with large, round, slipskin (pulp does not adhere to the flesh) berries with a foxy flavor that ripen approximately one week after the instant variety. Arkansas selection 1672 is a seedless, green or white-fruited grape with large, oval, non-slipskin (pulp adheres to the flesh) berries with a muscat flavor, that ripen approximately one week after the instant variety. Both of the parents of the instant cultivar are hybrids of the grape genus and species *Vitis labrusca* L. and *Vitis vinfera* L. Thus the instant cultivar is also of this two-species genetic background. The seeds resulting from this controlled hybridization were germinated in a greenhouse during the winter of 1981–82. Resulting seedlings were planted in the spring of 1982 in a vineyard on the Arkansas Agricutural Experiment Station at Clarksville, Ark. The seedlings fruited in the summer of 1984 and one, designated Ark. 1985, was selected for its large seedless fruits, unique muscat flavor, and good fruit quality.

During 1984, the original plant selection was propagated asexually at Clarksville, Arkansas by rooting hardwood cuttings and a test planting of three vines was established. Subsequently, larger test plantings have been established with asexually multiplied vines at two additional locations in Ark. and on state agricultural experiment stations in Athens, Ga. USA, West Lafayette, Ind. USA, and Pelotas, Rio Grande do Sul, Brazil. In all propagations hardwood cuttings were used and the instant cultivar roots readily from hardwood cuttings. All propagules (resulting plants) of the instant cutivar have been observed to be true to type in that during all asexual multiplication, the vegetative and fruit characteristics of the original plant have been maintained. All vines planted from hardwood cutting propagation fruited in the third season of growth in the vineyard after planting.

Test plantings over a wide geographic area have shown this new variety to be widely adapted to differing soil and climatic conditions. It has shown moderate winter hardiness during cold winters, being more hardy than the cultivars 'Einset Seedless' (U.S. Plant Pat. No. 6,160), 'Canadice' (non-patented), 'Himrod' (non-patented), 'Saturn' (U.S. Plant Pat. No. 6,703), 'Vanessa Seedless' (non-patented), and 'Venus' (non-patented), but less hardy than the cultivars 'Mars' (U.S. Plant Pat. No. 5,680) and 'Reliance' (U.S. Plant Pat. No. 5,174). It is not as sensitive to 2,4-D herbicide injury as the cultivars 'Mars', 'Sunbelt' (U.S. Plant Pat. No. 8,511), and 'Remaily Seedless' (non-patented).

Vines of the new variety have medium vigor, with a procumbent growth habit characteristic of *Vitis labrusca* (a comparative species). Vigor, as reflected in dormant pruning weights measured on mature vines, indicated that the instant cultivar was less vigorous than 'Mars', and near comparable in vigor to that of 'Venus'. Also, vine size as determined on vines growing on a Four-Arm Kniffin trellis with the top wire of this trellis placed at a height of 4 ft. 10 in., indicated a vine height of 5 ft. 5 in. an a vine spread of 2 ft. 6 in. It has produced well as own-rooted plants in all locations tested.

The new variety is moderately resistant to most common fungus diseases of grapevines. Under normal chemical disease control programs, the vines and fruit have demonstrated good freedom from black rot (*Guignardia bidwellii* (Ell.) V. & R.), anthrancnose (*Elsinoe ampelina* (d. By.) Sher), and powdery mildew (*Uncinula necator* Burr.), but it is susceptible to downy mildew (*Plasmopora viticola* Berl. & Tomi.) which is controllable by the use of available fungicides. The fruit has shown no inclination to split following rains.

The new variety ripens its fruit in early midseason, five days later than the early maturing 'Venus' cultivar but five and twelve days earlier than 'Reliance' and 'Mars', respectively. The average ripening date is July 24 in central Arkansas. The fruit quality is maintained well on the vine after maturity. Fruit of sound quality for marketing is maintained for up to two weeks on the vines after initial maturity is reached. Berries adhere well to the fruit pedicel and do not shatter from the clusters during this time.

The fruit is reddish blue in color at early maturity and becomes completely blue when fully mature. It is evenly colored within the cluster. The fruit shape is oval to slightly oblong. Fruit skins are medium thick and adhere to the flesh. The berries are large in size (ca. 5.5 g). The flavor is a mild muscat, and has been consistently rated high. Soluble solids concentration of the juice at fruit maturity average 19.8% with pH of 3.50. The fruit is of the stenospermocarpic type of seedlessness and contains small, soft vestigial seed traces that are not noticeable when eaten. The berries are large in size for a seedless grape, averaging twice the size of the 'Mars' and 'Reliance' cultivars.

Fruit clusters, borne usually two per shoot, are medium in size (ca. 257 g), well-filled, but not overly tight. Fruit cluster peduncles are medium-long and easy to remove from the supporting shoots during harvest.

The new variety has been named the 'JUPITER' cultivar.

BRIEF DESCRIPTION OF THE PHOTOGRAPHS

The accompanying photographs show typical specimens of the fruit FIG. 1) and leaf (FIG. 2) of the new variety in color as nearly true as it is reasonably possible to make in a color illustration of this character.

DETAILED DESCRIPTION OF THE NEW VARIETY

The following is a detailed description of the botanical and pomological characteristics of the subject grapevine. Color data are presented in Royal Horticultural Society Colour Chart designations and are supplemented with readings from a Minolta Chroma Meter CR-200, version 3.0, which measures absolute chromaticity in tristmulus values Y, x, and y. Calibration was performed using a standard white plate supplied by the manufacturer.

Where dimensions, sizes, colors and other characteristics are given, it is to be understood that such characteristics are approximations of averages set forth as accurately as practicable.

The descriptions reported herein are from specimens grown at Clarksville, Ark. Vines used for measurement were grown on a Linker fine sand loam soil and the vines were irrigated using trickle (drip) irrigation. The majority of the data collection was from vines that were 12 years old. Floral characteristics and measurements were observed at anthesis (full bloom).

Vine:

*Size.*—Large; vine size as determined on vines growing on a Four-Arm Kniffin trellis with the top wire of this trellis placed at a height of 4 ft. 10 in., indicated a vine height of 5 ft. 5 in. and a vine spread of 2 ft. 6 in.

*Growth.*—Medium vigor; comparative vigor as measured by weighing prunings at dormant pruning with pruning severity to a standard formula of 30+10 (thirty buds left on the vine for the first one pound of prunings and 10 buds left for each subsequent pound of prunings) indicated a pruning weight of 'Jupiter' of 2.0 lb, 'Mars' 4.1 lb, and 'Venus' 1.8 lb. Bud break March 25, growth cessation in early fall.

*Productivity.*—High (25–29 t/ha on mature vines).

*Cold hardiness.*—Hardy to −23° C.

*Canes.*—Medium diameter, not upright in growth habit. Diameter of mature cane: base 0.99 cm, midpoint 0.63 cm, terminal 0.19 cm. Internode length: base 6.89 cm, midpoint 9.33 cm, terminal 3.60 cm. Color of mature cane: base Greyed-Orange Group (165A) Y=11.59, x=0.3930, y=0.3490; midpoint Greyed Orange Group (165B) Y=23.56, x=0.4403, y=0.3858; terminal Greyed-Orange Group (165B) Y=20.55, x=0.4220, y=0.3738; no anthocyanin observed on mature canes; lenticels present on mature canes and are numerous, scattered and small (less than 0.5 mm in diameter). Annual pruning of canes is required for reliable production. Diameter of young shoots in spring (measured when shoots are 6–12" long); base 6.0 mm, midpoint 4.0 mm, terminal 2.0 mm. Internode length 55.0 mm. Shoot tips (from the terminal to 4–5 nodes from the terminal) have anthocyanin present in the shoots varying from solid red color to striping of red on the shoot tips.

*Tendrils.*—Total length averages 13 cm; texture smooth; usually forked and curled on distal end. Color of mature tendril is Greyed-Orange Group (177A). Tendrils found beginning opposite node 4 then again at nodes 6, 7, 9, 10 with this repeating intermittent pattern to the distal end of the cane.

*Buds.*—Average number of buds on a current, single-season growth cane is 28; dormant bud (compound bud or eye) width 5.0 mm; shape triangular; color Brown Group (200B); texture smooth.

*Disease resistance.*—Moderate resistance to fungus diseases black rot, powdery mildew, and anthracnose; Susceptible to downy mildew.

*Insect resistance.*—Insecticides were applied to the vines under evaluation to control climbing cutworms, grape berry moth and green June beetle. No resistances to these pests were determined in these evaluations due to chemical control of these pests.

Foliage:

*Leaves.*—Leaves simple and alternate; shape ovate to suborbicular; number of lobes 3; petiole sinus shape half open; venation palmate-pinnate; margin serrated with shape of teeth rectalinear and teeth short or medium in size. Color of mature leaves: base abaxial-Yellow-Green Group (147B) Y=17.51, x=0.3527, y=0.4102; adaxial-Green Group (137B) Y=9.74, x=0.3357, y=0.3945; midpoint abaxial-Yellow-Green Group (147B) Y=18.65, x=0.3442 y320.3982; adaxial-Green Group (137B) Y=9.39, x=0.3319, y=0.3949; terminal abaxial-Yellow-Green Group (147B) Y=20.40, x=0.3468, y=0.4146; adaxial-Green Group (137B) Y=12.95, x=0.3448, y=0.4311. No anthocyanin on upper or lower surfaces of leaves or on leaf veins. Color of mature petioles Green Group (141D). Petiole anthocyanin present on entire surface on young leaves with decreasing anthocyanin intensity as leaves age, with anthocyanin absent on oldest leaf petioles. Mature leaf petiole length is 11.75 cm. Sinus of mature leaf is 5.20 cm deep and 2.54 cm at widest point. Mature leaves are glabrous on the abaxial surface; pubescence on the adaxial surface is of medium density, prostrate, and present on the area between the main veins. Light, prostrate pubescence is found on the adaxial surface of newly-emerged leaf petioles with glabrous petioles on fully-expanded leaves. Color of young (unfolded) leaves: base abaxial Green Group (143A) Y=21.84, x=0.3511, y=0.4138; adaxial Yellow-Green Group (146A) Y=14.89, x=0.3507, y=0.4349; midpoint abaxial-Green Group (135C) Y=24.08, x=0.3589, y=0.4165; adaxial-Yellow-Green Group (147B) Y=18.17, x=0.3661, y=0.4463; terminal abaxial Yellow-Green Group (153C) Y=42.15, x=0.3454, y=0.3690; adaxial-Yellow-Green Group (152D) Y=30.73, x=0.3771, y=0.4164. Petiole color of young leaves Yellow-Green Group (146D).

Flowers: (as measured at the time of full bloom/anthesis):

*Inflorescence.*—Panicle.

*Date of bloom.*—First: May 11; Last: May 24.

*Shape of cluster.*—Conical, with occasional shoulder.

*Size of cluster.*—Length: 12.5 cm. Width: 7.5 cm

*Number of flowers per cluster.*—355.

*Individual entire flower dimensions.*—3.8 mm length, 2.00 mm width.

*Petal number.*—5, fused in calyptra.

*Petal color.*—Yellow-green group (145A).

*Petal shape.*—Cohering at the summit, separating at the base; 3.1 mm long, 1.3 mm wide at fused end; separated end reflexed after dehiscence from flower.

*Sepal number.*—5, flat round with lobes.

*Sepal color.*—Yellow-green group (145A).

*Flower fragrance.*—Yes.

Reproductive organs:

*Stamen number.*—5.

*Stamen color.*—Filament: white group (155A); Anther freshly opened greyed-yellow group (162B).

*Pistil number* (*individual flower*).—1.

*Pistil length.*—3.0 mm.

*Pistil color.*—Yellow-green group (145A).

*Pollen amount.*—Normal.

*Pollen fertility.*—Normal.

*Pollen color.*—Yellow-green group (158C).

Fruit:

*Maturity.*—Early midseason, five days after 'Venus'. Average ripe date is July 24. Even ripening in cluster.

*Size.*—Large, avg. 5.5 g, uniform in size.

*Shape.*—Oval to slightly oblong, uniform.

*Color.*—Reddish Blue at maturity, Purple Group (79A), Y=5.36, x=0.3143, y=0.3105.

*Texture.*—Semi-crisp.

*Skin.*—Medium thick, adhering to flesh (non-slipskin), semi-crisp.

*Character of seeds.*—Stenospermocarpic seedless, small vestigial seeds present but not lignified and unnoticeable when eaten.

*Brush length.*—4.5 mm.

*Peduncle length.*—4.5 cm.

*Flavor.*—Mild muscat, sweet.

*Soluble solids.*—19.8% .

*pH.*—3.50.

*Mature cluster weight.*—257 g.

*Berries per cluster.*—48–61, $\bar{x}$=56.

*Clusters per vine.*—75–151, $\bar{x}$=114.

*Clusters per shoot.*—Usually 2.

*Uses.*—Fresh consumption when seedlessness and muscat flavor is desirable. No wine nor raisin evaluations have been done on 'Juptiter'.

The variety: The most distinctive features of the variety are its large, seedless berries, excellent muscat flavor, resistance to fruit cracking, good productivity, and good vine hardiness.

We claim:

1. A new and distinct variety of grape plant, substantially as illustrated and described, characterized by its large, seedless berries, excellent muscat flavor, resistance to fruit cracking, good productivity, and good vine hardiness.

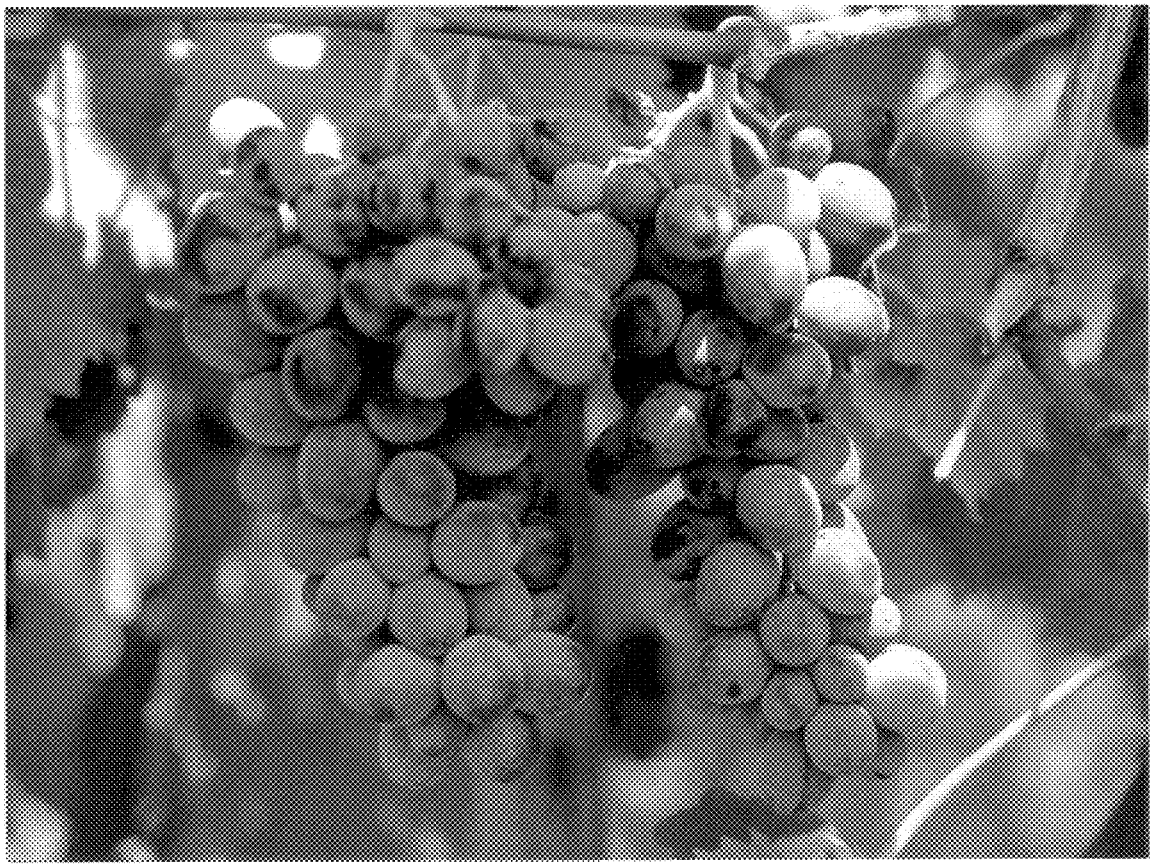

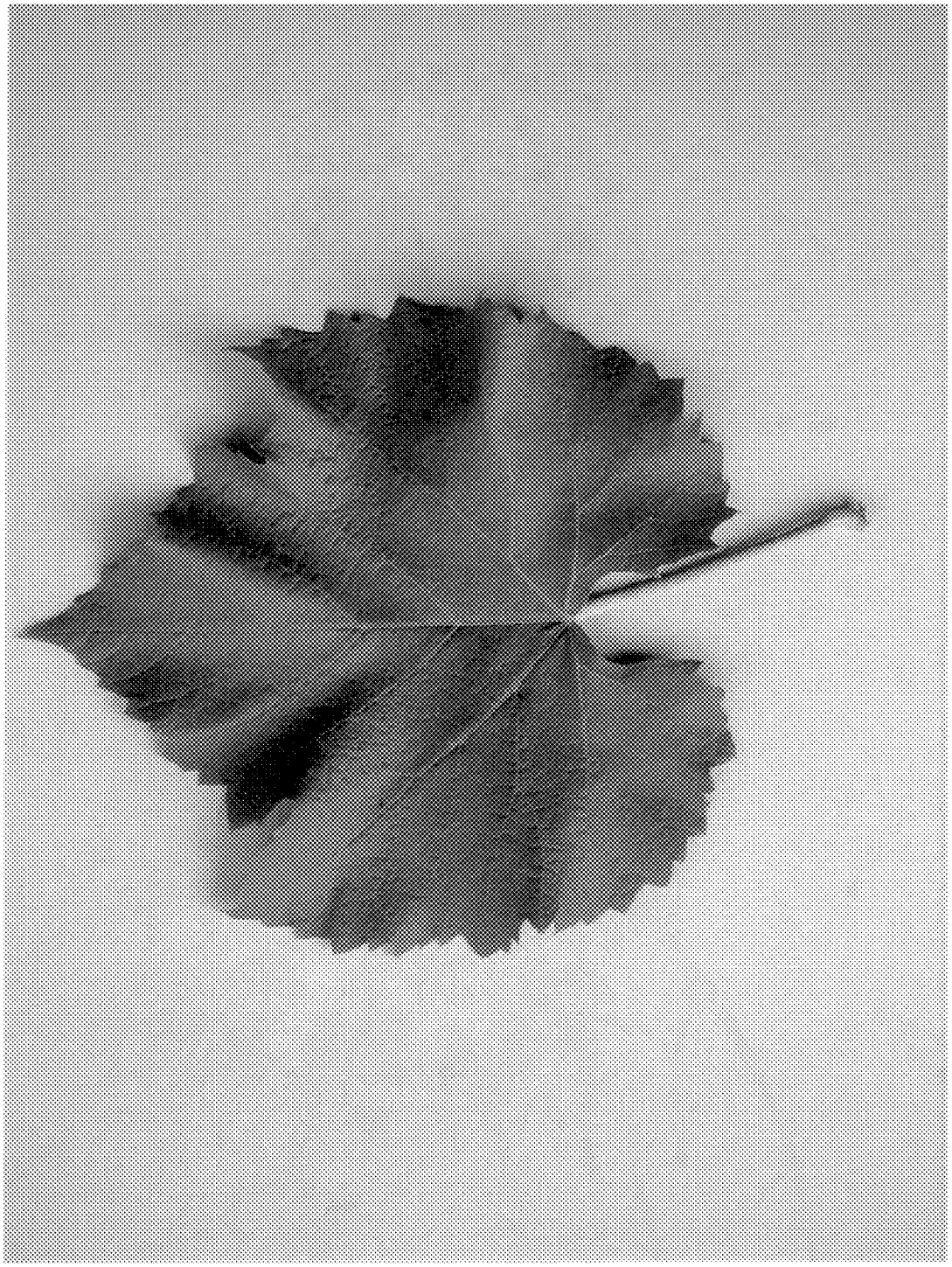

* * * * *